Figure 1:
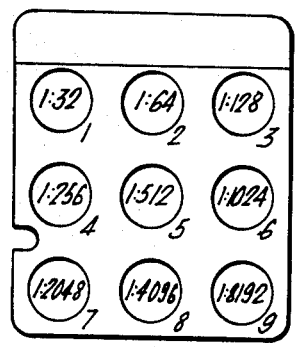

United States Patent [19]

Suovaniemi

[11] 4,290,997
[45] Sep. 22, 1981

[54] APPARATUS FOR AUTOMATIC MEASUREMENT OF THE RESULTS OF AGGLUTINATION TESTS

[75] Inventor: Osmo A. Suovaniemi, Helsinki, Finland

[73] Assignee: Kommandiittiyhtio Finnpipette Osmo A. Suovaniemi, Finland

[21] Appl. No.: 15,316

[22] Filed: Feb. 26, 1979

[30] Foreign Application Priority Data

Feb. 28, 1978 [FI] Finland ............................ 780670

[51] Int. Cl.$^3$ ...................... G01N 1/00; G01N 33/54; G01N 35/00
[52] U.S. Cl. .................................. 422/73; 23/230 B; 356/246; 422/63; 422/102
[58] Field of Search ................... 23/230 B; 422/72, 73, 422/102; 356/246; 424/11, 12

[56] References Cited

U.S. PATENT DOCUMENTS

| | | | |
|---|---|---|---|
| 3,707,354 | 12/1972 | Goodman | 422/11 X |
| 3,883,308 | 5/1975 | Matte | 356/246 X |
| 3,955,923 | 5/1976 | Asculai | |
| 4,144,030 | 3/1979 | Suovaniemi | 356/246 X |
| 4,148,607 | 4/1979 | Bernoco | 422/72 X |

FOREIGN PATENT DOCUMENTS

| | | |
|---|---|---|
| 2009524 | 2/1970 | France |
| 588700 | 6/1977 | Switzerland |
| 1229971 | 4/1971 | United Kingdom |
| 1377658 | 12/1974 | United Kingdom |
| 1486210 | 9/1977 | United Kingdom |
| 1532057 | 11/1978 | United Kingdom |

OTHER PUBLICATIONS

Sargent-Welch Catalog, pp. 224 and 1075, Skokie, IL; 1971.

Primary Examiner—Sidney Marantz
Attorney, Agent, or Firm—Hopgood, Calimafde, Kalil, Blaustein & Judlowe

[57] ABSTRACT

A method and an apparatus for automatic measurement of the results of agglutination tests, e.g., in a spectrophotometer, adsorption photometer, fluorometer, or nephelometer. Samples of agglutination tests are incubated in reaction vessels, such as cuvettes or set of cuvettes, so as to inactivate the samples before measurement. During incubation of the samples, the reaction vessels are placed, either by sufficient inclination of the reaction vessels or by using reaction vessels specifically designed for the purpose, in which reaction vessels the bottom construction of the reaction vessel has a recess that is positioned lower than the point of passage of the measurement beam, i.e. the measurement window, in the bottom part of the reaction vessel, into such a position that, when no agglutination has taken place, the non-agglutinated particles are assembled or heaped in the reaction vessels into their parts or recesses placed at the lowest level, outside the route of passage of the beam of measurement. When agglutination takes place, it is formed in the reaction vessels at the position through which the beam of measurement passes.

2 Claims, 9 Drawing Figures

APPARATUS FOR AUTOMATIC MEASUREMENT OF THE RESULTS OF AGGLUTINATION TESTS

The subject of the present invention is a method and an apparatus for automatic measurement of the results of agglutination tests, e.g., in a spectrophotometer, adsorption photometer, fluorometer, or nephelometer, whereby samples of agglutination tests are incubated in reaction vessels, such as cuvettes or set of cuvettes, so as to inactivate the samples before measurement.

Various agglutination tests are used in order to demonstrate certain, e.g., bacteria, viruses, fungi, or their antibodies and antigen components, as well as some abnormal proteins. Among these tests should be mentioned the HA-test (hemagglutination test), HAI-test (hemagglutination inhibition test), IHA-test (indirect hemagglutination test), cold agglutinins test, and LA-test (Latex agglutination test).

The above tests are used in serologic identification, serotyping, and serodiagnosis. Said tests are highly usable, e.g., in epidemy studies and classifications.

The IHAI-test is also suitable for establishing pregnancy by demonstration of HCG (human chorionic gonadotropin) hormone secretion into the urine. Further, e.g., the HAI-test is used for determination of blood group.

Depending on the test used, agglutination may mean either positive or negative result. E.g., hemagglutination can be ascertained on the bottom of the reaction vessel as a diffuse cover. E.g., in the HA-test, certain viruses and bacteria have the ability to precipitate red blood corpuscles under certain circumstances onto the bottom of the reaction vessel on a large area. If no hemagglutination takes place, the red blood corpuscles are usually assembled in the reaction vessel into an area or a button with distinct borders.

The results of agglutination tests have been read visually. In different tests the criteria of interpretation of the tests show variation. As the results are read visually, many different error factors are involved. Different people see in different ways, the eye easily becomes tired, and the results may change, human error factors are high in the interpretation and output of the results, etc. It is also possible to include a certain colour indicator in agglutination tests, whose visual interpretation in a negative or positive test is laborious. If a fluorescent substance is included in the tests, many advantages are obtained when the test results are measured fluorometrically. Nephelometric measurement of some test results increases the possibilities and advantages. From the above it is already easy to understand that visual interpretation of the results is restrictive and unreliable.

Similar tests are used abundantly in different fields. Often it is multiple tests that are concerned, such as syphilis and rheumatism test, blood group determinations, and establishment of pregnancy. In such cases, performance of the tests must be simple, automatic, precise, and reliably reproducible, among other things.

So far, there is no simple and reliable automatized way of performing the above tests. A highly complicated and expensive set of equipment (Groupamatic, about 1.5 million Fmks.) is available, e.g., for blood group determinations. The circumstance that it has not been possible to construct a simple and automatic measurement device of reasonable cost for different types of agglutination tests results, e.g., from the fact that methods suitable for automation have not been discovered.

The circumstances characteristic of the invention come out from the patent claims.

The method and the apparatus in accordance with the present invention permit the measurement of the results of different agglutination tests, e.g., in spectrophotometer, adsorption photometer, fluorometer, and nephelometer so that the agglutination is formed in the reaction vessel at such a position through which the measurement beam passes so that the measurement beam does not meet non-agglutinated particles when no agglutination has taken place.

Figure 2:
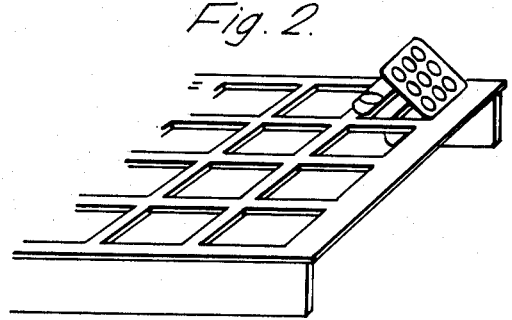
Figure 3:
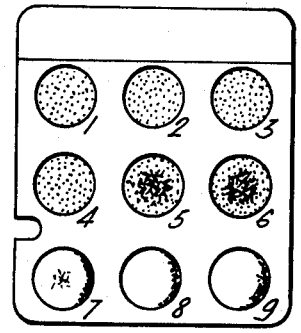
Figure 4:
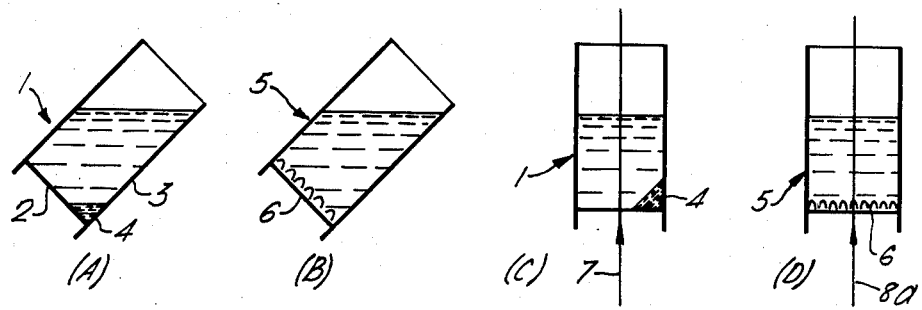
Figure 5:
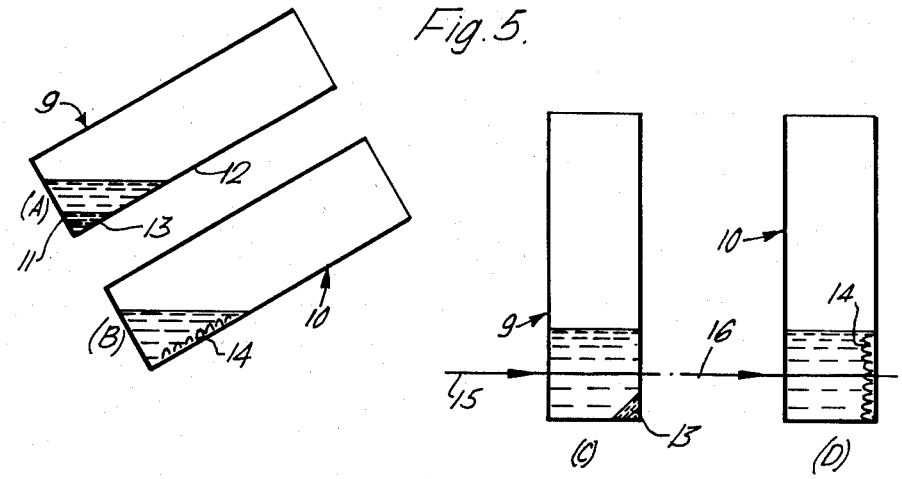
Figure 6:
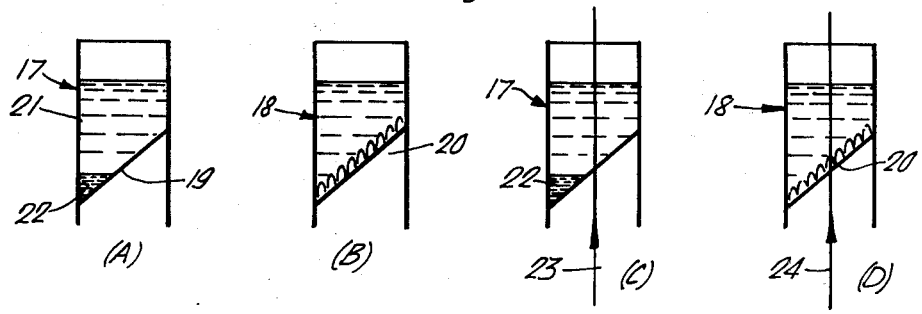
Figure 7:
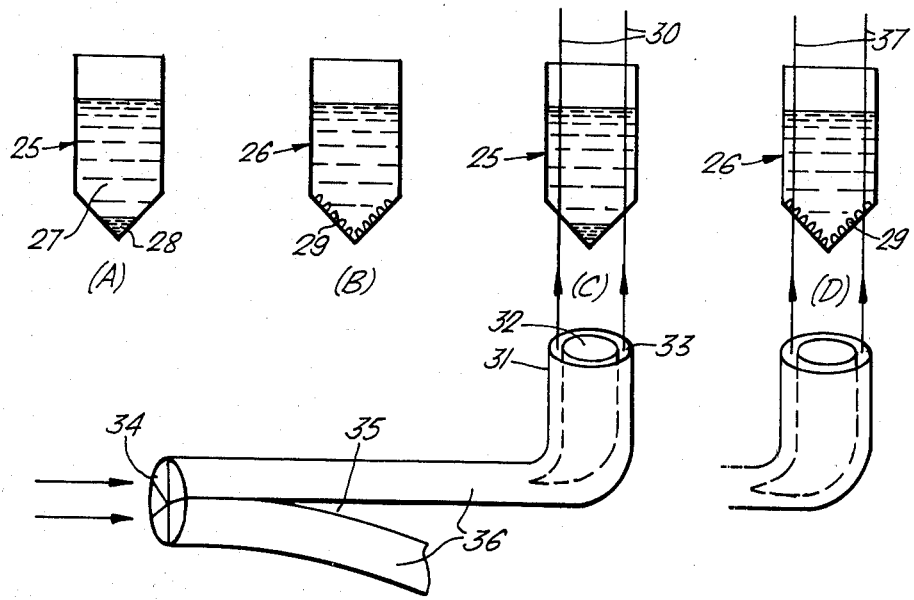
Figure 8:
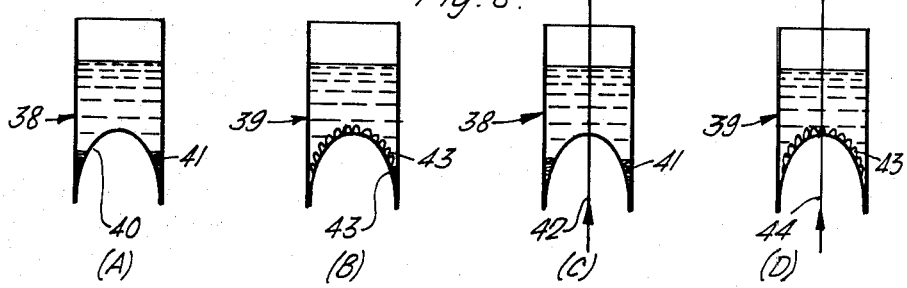
Figure 9:
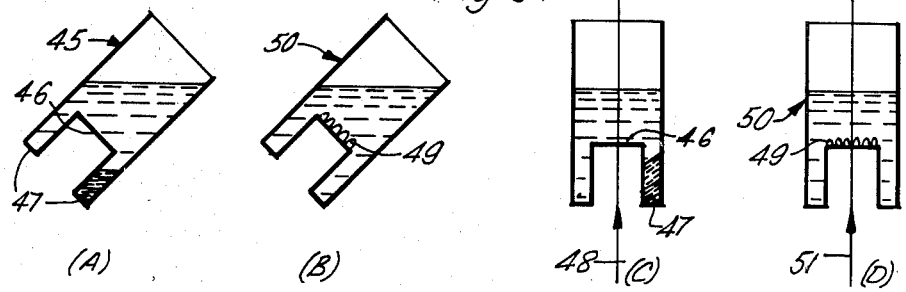

The invention comes out more closely from the following description and from the attached drawings, wherein FIG. 1 shows, as related to the exemplifying embodiment, a serum dilute pipetted into the set of cuvettes, FIG. 2 shows the inclined position of the set of cuvettes during incubation, FIG. 3 shows the set of cuvettes together with the samples as viewed from above during a test, FIGS. 4 and 5 show the performance of the method in accordance with the invention by means of inclination of the cuvette in connection with vertical and horizontal measurement, FIG. 6 shows an apparatus in accordance with the invention for the performance of the method, and FIGS. 7 to 9 show embodiments alternative to the apparatus shown in FIG. 6.

Below, an exemplifying embodiment of the method in accordance with the present invention is described.

Waaler-Rose assay by means of FP-9 analysing equipment

Principle:

The rheumatoid factor (RF) is an IgG auto-antibody belonging to class IgM. RF reacts with IgG derived from man.

Reagents:

The operating reagent contains:
1. Ambocepter (serum of rabbit) as diluted 1:1000 by means of 0.9% NaCl. The serum of rabbit is inactivated before use by incubation at +56° C. for 30 minutes.
2. 0.9% NaCl
3. Red corpuscles of human ORh+ group that have been washed 5 to 6 times with 0.9% NaCl.
4. Normal serum pool.

Two basic solutions are prepared:

Solution A:
  13.5 ml 0.9% NaCl
  1.2 ml normal serum pool
  0.15 ml washed human ORh+ red corpuscles (1 to 2% suspension in 0.9% NaCl). Are stirred gently.

Solution B:
  9.5 ml 0.9% NaCl
  0.5 ml 1:1000 diluted ambocepter.

Operating solution:
  10 ml of solution A are added to 10 ml of solution B. The mixture is allowed to stand for 10 to 15 minutes at the room temperature, whereby the ambocepter adheres to the surface of the red corpuscles. Thereupon the solution is ready for use.

Performance:
1. The patient samples are inactivated by incubation at +56° C. for 30 minutes.
2. Nine dilutions are made of each sample into a set of test tubes. 0.9% NaCl is used as diluent.

3. 0.2 ml of each serum dilution is pipetted into the cuvette set in accordance with what is shown in FIG. 1.
4. 0.2 ml of the operating solution are added.
5. The cuvette sets are incubated at +4° C. for at least 4 hours while the cuvette sets are at an angle of about 45° (FIG. 2). The incubation may be continued overnight.
6. The results are read in FP-9 photometer. The absorbences are measured from the cuvette set against distilled water at the wave length of 600 nm.

Agglutinated red corpuscles cover the bottom of the cuvette and give an absorbence, whose magnitude depends on the thickness of the layer of cells. If there is no rheumatoid factor in the serum, no agglutination takes place and the red corpuscles fall freely and, owing to the slanting position, assume a narrow front position on one side of the cuvette bottom.

EXAMPLE

The set of cuvettes shown in FIG. 3 gave the following absorbences when measured:

ABS.
1. 0.571
2. 0.603
3. 0.623
4. 0.603
5. 0.465
6. 0.222
7. 0.141
8. 0.059
9. 0.048

Cuvette no. 7 is the last one in which the absorbence is above the base level (cuvettes 8 and 9). Cuvette 7 has the dilution of 1:2048. Thus, in this case the titre of the RF is 2000.

The results obtained by means of the FP-9 analysing system from the Waaler-Rose assay correlate well with the results obtained with Mikrotiter-equipment when the same reagents and incubation conditions are used.
Interpretation of results:

The end point of the titration is the inverted value of dilution in the last cuvette that gives a higher absorbence (agglutination) than the base level (clear solution).

In the above example the agglutination has been measured by using the principle of vertical measurement of the FP-9 system (The Finnpipette$^R$ Analyzer System). When the reaction has been allowed to take place in an inclined cuvette set block before measurement, the agglutination has been formed onto the cuvette bottoms through which the measurement beams pass. In this case, it is most appropriate to incline the cuvette set block 15° to 60°.

If the measurement beam passes perpendicularly to the longitudinal axis of the cuvette, i.e. the measurement takes place by means of a horizontal measurement beam, the cuvettes must be inclined more than in the former case. In this case, agglutination is produced on the cuvette wall, i.e. at the position through which the measurement beam passes. The most appropriate angle of inclination is less than 90°. After the agglutination reaction the cuvette or cuvettes are turned into vertical position, whereby in the reaction in which no agglutination took place the red corpuscles or some other particles to be agglutinated pass more completely onto the bottom of the cuvette. Then, the optical window, through which the measurement beam passes, remains free from particles that were not agglutinated.

To the position on the cuvette at which the produced agglutination is measured, it is also possible to attach specific antigens or antibodies for the agglutination complex, in which case the agglutination complex adheres to the cuvette wall or bottom more firmly by the intermediate of these antigens or antibodies. Then, if necessary, it is easy to wash free red corpuscles or any other particles off from the cuvette so that the agglutinated complex is not removed by washing.

Moreover, it is possible to attach a colouring or fluorescent agent or any other measurable agent to the agglutination complex, whereby it is possible to increase the ability of separation of the measuring technique.

A cuvette may also be constructed so that its bottom is appropriately at a certain angle. In such a case, the cuvette may be kept in vertical position, because the bottom has the desired angle of inclination.

The measuring device may also be constructed so that the measuring beam has a limiter at the position at which the non-agglutinated particles are assembled.

The following FIGS. 4 to 9 show, out of the method in accordance with the present invention, certain exemplifying embodiments of reaction vessels in which the agglutination reactions can be measured. The measuring vessels are separate cuvettes, or they may be placed into a matrix comprising several cuvettes. Such matrices may also be manufactured by means of transfer-moulding out of plastics, like the cuvette block of the FP-9 system.

In FIG. 4, the cuvette 1 is at a certain angle (preferably 15° to 60° in relation to the vertical level) during the reaction. In case A (FIG. 4) no agglutination has taken place, so that the red corpuscles or other particles sink into the angle 4 formed by the cuvette bottom 2 and the wall 3.

In case B, on the contrary, agglutination has been formed, and the agglutinated particles have formed a uniform and dim mat on the entire bottom 6 of the cuvette 5.

When the cuvettes 1 and 5 are in vertical position (FIG. 1, C and D) and are measured by the principle of vertical measurement, wherein the measurement beams 7 and 8 pass vertically and as parallel with the longitudinal axes of the cuvettes 1 and 5, respectively, the measurement beam 8 reaches only the agglutination 6 on the bottom of the cuvette 5. The measurement beam 7 does not reach the non-agglutinated particles in the angle 4 formed by the cuvette 1 bottom 2 and wall 3, whereby the intensity of the measurement beam 7 remains as high as the reference value. This mode of measurement also permits detection of different degrees of agglutination, as is indicated, e.g., by the measurement results of the above Waaler-Rose agglutination test.

FIG. 5 shows the same steps as in FIG. 4, as presented in a cuvette of different type, in which the measurement is performed by the principle of horizontal measurement, in steps C and D.

In the reaction steps A and B, the cuvettes 9 and 10 are inclined (less than 90°). In step A, no agglutination has been produced, so that the particles have sunk into the angle 13 between the cuvette bottom 11 and wall 12. In case B, agglutination has been formed on the cuvette 10 wall 14.

When measurement is performed by the principle of horizontal measurement, wherein the measurement beams 15 and 16 pass perpendicularly to the longitudinal axes of the cuvettes 9 and 10, respectively, the measurement beam 15 does not meet the non-agglutinated particles in the corner 13 of the cuvette 9 (FIG. 2, C). On the contrary, the agglutination that has adhered to the wall 14 of the cuvette comes into the way of the measurement beam 16 and causes a change in the measurement result (FIG. 2, D). If the reaction mixture is removed from the cuvette, the agglutination adhered to the cuvette wall may also be coloured by means of an appropriate colouring solution, which may also improve the adhesion of the agglutination to the wall. If colouring of the agglutination is used, the test becomes more sensitive and the ability of separation is improved, because the measurement can be performed, e.g., in a photometer at a wave length absorbing the colouring agent.

The cuvettes 17 and 18 shown in FIG. 6 are constructed so that the bottom of the cuvette is at a certain angle (preferably 15° to 60°) in relation to the cuvette wall. Then, when the cuvette 17 is in the vertical position, the non-agglutinated particles are sedimented in the angle 22 formed by the cuvette 17 wall 21 and bottom 19 (FIG. 6, A). In cuvette 18 the agglutinated particles have been assembled to the surface of the cuvette bottom 20 (FIG. 6, B).

When the cuvettes 17 and 18 are measured by means of vertical measurement beams 23 and 24 (FIG. 6, C and D), the measurement beam 24 meets only the agglutinated particles on the cuvette 18 bottom 20. On the contrary, the measurement beam 23 in cuvette 17 (FIG. 6, C) does not meet the non-agglutinated particles in the angle 22. The cuvette bottoms may be, e.g., plane, plane-convex, convex-convex, convex-concave, or concave-convex. Such cuvettes may, e.g., be individual, they may be placed into a certain matrix, or they may be transfer-moulded out of plastics into a matrix including many cuvettes.

FIG. 7 shows the cuvettes 25 and 26, which may have, e.g., V-shaped or U-shaped bottoms. Non-agglutinated particles are sedimented in the tip portion 28 of the V-bottom 27 of the cuvette 25 (FIG. 7, A). The agglutinated particles are positioned on the wall 29 of the V-bottom of cuvette 26 (FIG. 7, B).

When a cuvette 25 in which the non-agglutinated particles are in the tip 28 of the bottom is measured by means of the vertical measurement principle, wherein the measurement beams pass as a cylinder 30 of appropriate size around the longitudinal axis of the cuvette (FIG. 7, C), these measurement beams 30 do not meet the particles in the tip 28 of the cuvette.

On the contrary, when, in the case of FIG. 7, D, the cuvette 26 is being measured, the agglutinated particles on its bottom 29 come to lie in the way of the measurement beams 37.

The conductor 31 of the measurement beam has a core portion 32, which does not conduct measurement beams. The measurement beam passes at the end part of the measurement beam conductor as a cylindrical part 33. The conductor of such a measurement beam may be, e.g., a plastics, glass, or quartz fibre. The beginning 34 of this conductor exists as one bundle, and at the point of distribution 35 it may be divided into several separate conductors 36 of measurement beams. The end part of the conductor of measurement beam has a core portion 32 non-transparent to the measurement beam. When such a measurement beam conductor is used, whose end portion has been made cylindrical, no limiter is required in front of the measurement beam. A measurement beam conductor that is distributed into cylindrical form is helpful in making the measurement beam parallel without complicated lense systems between the measurement beam conductor and the cuvette bottom.

FIG. 8 shows cuvettes 38 and 39, whose bottoms may have different shapes, e.g. convex-concave and convex-convex. In such a case the lense effect of the bottom may be used most appropriately for guiding the measurement beam through the bottom of the cuvette.

The cuvette 38 bottom 40 is convex-concave. Since no agglutination takes place, the non-agglutinated particles sink into the corner 41 between the bottom 40 and the wall of the vertical cuvette 38, whereby, during measurement, with the cuvette 38 standing vertically (FIG. 8, C), the measurement beam 42 does not meet the non-agglutinated particles in the corner 41. In cuvette 39 the agglutinated particles have positioned themselves as an even mass on the cuvette bottom 43, and when measurement is performed, the measurement beams 44 meet the agglutination on the cuvette 39 bottom 43 (FIG. 8, D).

In FIG. 9, section A, e.g., a cylindrical annular space 47 constitutes an extension of the cuvette 45 bottom 46. Then, when the cuvette 45 is at an appropriate angle of inclination, the non-agglutinated particles are carried into the cylindrical annular space 47. When the cuvette 45 is measured (FIG. 9, C), the measurement beams 48 pass through the cuvette 45 bottom 46 without meeting the particles in the cylindrical annular space 47 of the cuvette. When the cylindrical annular space 47 is sufficiently deep, the particles carried into same do not come readily back onto the cuvette bottom 46.

In section B, the agglutination is also formed on the bottom 49 of the cuvette 50. During measurement in section D, the measurement beams 51 meet the agglutination on the bottom 49 of the cuvette 50.

In the specification, the term "convex-concave" is meant to describe the bottom of a reaction vessel which has a concave upper surface and a concave lower surface. The term "concave-convex" is meant to describe a reaction vessel bottom which has a concave upper surface and a convex lower surface. The term "convex-convex" is meant to describe a reaction vessel bottom which has a convex upper surface and a convex lower surface. The term "concave-concave" is meant to describe a reaction vessel bottom which has a concave upper surface and a concave lower surface.

What we claim is:

1. An apparatus useful for the automatic measurement of the results of agglutination tests, said apparatus comprising at least one reaction vessel for the incubation of a sample to be tested prior to said testing, said reaction vessel having (a) at least one vertical side wall portion and a bottom portion, (b) at least one recess for receiving the non-agglutinated particles, said recess comprising an angle formed between said vertical side wall portion and said bottom portion, (c) an area for receiving the agglutinated particles such that said recess is out of the position of passage of a measurement beam which is adapted to measure the amount of agglutination which takes place within said reaction vessel, and (d) a measurement window for passage of said measurement beam, said apparatus being adapted for use in a vertical position.

2. An apparatus useful for the automatic measurement of the results of agglutination tests, said apparatus comprising at least one reaction vessel for the incubation of a sample to be tested prior to said testing, said reaction vessel having (a) a bottom portion wherein said bottom portion comprises a middle annular portion and an outer annular portion wherein said outer portion is lower than said middle portion when said vessel is in a vertical position and said measurement window is in said middle portion, (b) at least one recess for receiving the non-agglutinated particles, said recess being placed lower than the position of passage of said measurement beam in said bottom portion of said reaction vessel, (c) an area for receiving the agglutinated particles such that said recess is out of the position of passage of a measurement beam which is adapted to measure the amount of agglutination which takes place within said reaction vessel, and (d) a measurement window for passage of said measurement beam, said apparatus being adapted for use in a vertical position.

* * * * *